United States Patent
Steeves et al.

(10) Patent No.: US 8,074,650 B2
(45) Date of Patent: Dec. 13, 2011

(54) TRACHEOSTOMY TUBE HOLDER

(75) Inventors: Sharon Steeves, Bellingham, MA (US); Allison Frazer, Blackstone, MA (US); Ronald D. Russo, Barrington, RI (US)

(73) Assignee: Dale Medical Products, Inc., Plainsville, MA (US)

( * ) Notice: Subject to any disclaimer, the term of this patent is extended or adjusted under 35 U.S.C. 154(b) by 972 days.

(21) Appl. No.: 11/068,294

(22) Filed: Feb. 28, 2005

(65) Prior Publication Data
US 2005/0188993 A1   Sep. 1, 2005

Related U.S. Application Data

(60) Provisional application No. 60/548,406, filed on Feb. 27, 2004.

(51) Int. Cl.
*A61M 16/00*  (2006.01)
*A62B 9/04*   (2006.01)

(52) U.S. Cl. ......... 128/207.17; 128/207.14; 128/200.24; 128/202.27; 128/200.26

(58) Field of Classification Search ............. 128/202.27, 128/201.22, 201.23, 206.13, 206.21, 206.27, 128/207.11, 207.14–207.16, 207.17, DIG. 26, 128/876; 2/338, 908–911, 920, 52, 311, 2/312, 321; 24/3.4, 3.13, 265; 602/19; 604/174
See application file for complete search history.

(56) References Cited

U.S. PATENT DOCUMENTS

| | | |
|---|---|---|
| 2,865,069 A | 12/1958 | Gamble |
| 3,086,529 A | 4/1963 | Munz et al. |
| 3,535,719 A | 10/1970 | Murcott |
| 4,088,136 A | 5/1978 | Hasslinger et al. |
| 4,270,529 A | 6/1981 | Muto et al. |
| 4,313,437 A * | 2/1982 | Martin ..................... 128/207.17 |
| 4,326,515 A | 4/1982 | Shaffer et al. |
| 4,331,143 A | 5/1982 | Foster |
| 4,331,144 A | 5/1982 | Wapner |
| 4,351,331 A | 9/1982 | Gereg |
| 4,378,012 A | 3/1983 | Brown |

(Continued)

FOREIGN PATENT DOCUMENTS

| WO | WO 90/06735 A | 6/1990 |
|---|---|---|
| WO | WO 97/12552 | 4/1997 |

OTHER PUBLICATIONS

PCT International Search Report and Written Opinion of the International Searching Authority in International Application No. PCT/US2005/006346, May 17, 2005, 8 pages.

(Continued)

*Primary Examiner* — Justine Yu
*Assistant Examiner* — Annette Dixon
(74) *Attorney, Agent, or Firm* — Finnegan, Henderson, Farabow, Garrett & Dunner, LLP

(57) ABSTRACT

A tube holder is provided for securing a medical tube to a patient. In one illustrative embodiment, the tube holder includes a band to secure a medical tube to a patient, and first and second tabs attached at first and second ends of the band to secure the medical tube. Each of the first and second tabs include a hook surface and a loop surface, the hook surface and loop surface to mate with one another to secure the medical tube. The first and second tabs include moisture resistant material located on a surface contacting the patient's skin.

19 Claims, 8 Drawing Sheets

U.S. PATENT DOCUMENTS

| | | | |
|---|---|---|---|
| 4,437,463 A | 3/1984 | Ackerman | |
| 4,445,894 A | 5/1984 | Kovacs | |
| 4,449,527 A * | 5/1984 | Hinton | 128/207.17 |
| 4,520,813 A * | 6/1985 | Young | 128/207.17 |
| 4,537,192 A | 8/1985 | Foster | |
| 4,548,200 A | 10/1985 | Wapner | |
| 4,569,348 A | 2/1986 | Hasslinger | |
| 4,592,351 A | 6/1986 | Smith et al. | |
| 4,622,034 A | 11/1986 | Shattuck | |
| 4,658,814 A | 4/1987 | Anderson | |
| 4,744,358 A | 5/1988 | McGinnis | |
| 4,832,019 A | 5/1989 | Weinstein et al. | |
| 4,844,061 A | 7/1989 | Carroll | |
| 4,867,154 A | 9/1989 | Potter et al. | |
| 4,906,234 A | 3/1990 | Voychehovski | |
| 4,976,700 A | 12/1990 | Tollini | |
| 5,000,741 A | 3/1991 | Kalt | |
| 5,009,227 A * | 4/1991 | Nieuwstad | 128/207.17 |
| 5,015,251 A | 5/1991 | Cherubini | |
| 5,042,478 A | 8/1991 | Kopola et al. | |
| 5,058,579 A | 10/1991 | Terry et al. | |
| 5,060,645 A | 10/1991 | Russell | |
| 5,076,269 A | 12/1991 | Austin | |
| 5,101,822 A * | 4/1992 | Kimmel | 128/207.14 |
| 5,134,995 A | 8/1992 | Gruenke et al. | |
| 5,205,832 A | 4/1993 | Tuman | |
| 5,237,988 A * | 8/1993 | McNeese | 128/207.17 |
| 5,271,745 A | 12/1993 | Fentress et al. | |
| 5,295,480 A | 3/1994 | Zemo | |
| 5,305,742 A | 4/1994 | Styers et al. | |
| 5,306,233 A | 4/1994 | Glover | |
| 5,308,339 A | 5/1994 | Kalt et al. | |
| 5,341,802 A | 8/1994 | Calebaugh | |
| 5,357,952 A * | 10/1994 | Schuster et al. | 128/207.17 |
| 5,368,023 A | 11/1994 | Wolf | |
| 5,368,024 A | 11/1994 | Jones | |
| 5,402,776 A | 4/1995 | Islava | |
| 5,411,484 A | 5/1995 | Shattuck | |
| 5,437,273 A | 8/1995 | Bates et al. | |
| 5,471,980 A | 12/1995 | Varner | |
| 5,474,063 A | 12/1995 | Riendeau | |
| 5,485,837 A | 1/1996 | Solesbee et al. | |
| 5,490,504 A | 2/1996 | Vrona et al. | |
| 5,496,282 A | 3/1996 | Militzer et al. | |
| 5,501,216 A | 3/1996 | Byrd | |
| 5,529,062 A | 6/1996 | Byrd | |
| 5,551,421 A | 9/1996 | Noureldin et al. | |
| 5,558,090 A | 9/1996 | James et al. | |
| 5,671,732 A * | 9/1997 | Bowen | 128/207.17 |
| 5,672,159 A * | 9/1997 | Warrick | 604/179 |
| D393,310 S | 4/1998 | Russo | |
| 5,782,236 A * | 7/1998 | Ess | 128/207.17 |
| 5,803,079 A | 9/1998 | Rogers et al. | |
| 5,839,437 A * | 11/1998 | Briggs, III | 128/207.17 |
| 5,918,599 A | 7/1999 | Shesol | |
| 5,934,276 A | 8/1999 | Fabro et al. | |
| 5,967,144 A * | 10/1999 | Reynolds | 128/869 |
| 5,975,080 A | 11/1999 | Delaplane et al. | |
| 6,009,872 A | 1/2000 | Delaplane et al. | |
| 6,047,699 A * | 4/2000 | Ryatt et al. | 128/207.17 |
| 6,050,263 A | 4/2000 | Choksi et al. | |
| 6,067,985 A * | 5/2000 | Islava | 128/207.17 |
| 6,105,573 A | 8/2000 | Delaplane et al. | |
| 6,105,577 A | 8/2000 | Varner | |
| 6,158,584 A | 12/2000 | Knudsen | |
| 6,296,164 B1 | 10/2001 | Russo | |
| 6,408,850 B1 | 6/2002 | Sudge | |
| 6,412,117 B1 | 7/2002 | Holmes et al. | |
| 6,526,978 B2 | 3/2003 | Dominguez | |
| 6,561,192 B2 | 5/2003 | Palmer | |
| 6,578,576 B1 | 6/2003 | Taormina et al. | |
| 6,612,309 B1 | 9/2003 | Ancona | |
| 6,722,369 B1 | 4/2004 | Kron | |
| 6,779,525 B1 * | 8/2004 | Oganesian | 128/207.17 |
| 6,805,117 B1 * | 10/2004 | Ho et al. | 128/201.22 |
| 6,840,238 B1 | 1/2005 | Van Hegelsom | |
| 6,994,088 B2 * | 2/2006 | Briggs, III | 128/207.17 |
| 2002/0072656 A1 | 6/2002 | Vantassel et al. | |
| 2002/0139372 A1 | 10/2002 | Shikani | |
| 2003/0034036 A1 | 2/2003 | Waldeck | |
| 2004/0060565 A1 | 4/2004 | Kron | |
| 2005/0188993 A1 | 9/2005 | Steeves et al. | |

OTHER PUBLICATIONS

Thomas™ "Tracheostomy Strap," Part No. 600, product brochure (undated).
Thomas™ Tracheostomy Strap II, STI Medical Products, product brochure (undated).
Pepper Medical "Tracheostomy Tube Neckband," Product No. 301, product brochure (undated).
Thomas™ "Tracheostomy Strap Product Matrix," STI Medical Products, product Nos. 600, 675, 680 and 685, product brochure (undated).
A-T Surgical Mfg. Co., Inc., "A-T Nasogastric Tube Holder" product packaging (undated).
A-T Surgical Mfg. Co., Inc., "Suspensories," "Surgical Shield," "Catheter Leg Tube Holder," "Tracheostomy Tube Holder," "Catheter Waist Tube Holder," "Sweat Band," and "Nasogastric Tube Holder," product catalog (undated).
Ackrad Laboratories, Inc., "COMFIT™ Endotracheal Tube Holder," product brochure (1995).
Ackrad Laboratories, Inc., "COMFIT™ Endotracheal Tube Holder," product brochure (1999).
Advantage Medical, "Inside Advantage, Cath-Control™, catheter tube holder," product brochure (undated).
Ambu Inc., "Ambu® ET Tube Holder," product brochure (undated).
Anago®, "Cath-Control™ catheter anchor," product packaging (undated).
Ansley, a division of Struckmeyer, "tube holders," product brochures (undated).
B&B Medical Technologies, Inc., "B&B E.T. Tape" and "B&B E.T. Tape II," product brochures (undated).
B&B Medical Technologies, Inc., "B&B StabilTube," product brochure (undated).
B&B Medical Technologies, Inc., "B&B Lock-Tite," product brochure (undated).
B&B Medical Technologies, Inc., "B&B TrachGuard™," product information at http://www.bandb-medical.com (2005).
B&B Medical Technologies, Inc., "B&B Trachstay," product information at http://www.bandb-medical.com (2005).
B&B Medical Technologies, Inc., "Nasel E.T. Tape Kit™" and "Lock-Tite™," product advertisements (1996).
BrightWake Ltd., "tube holders," product information at http://www.brightwake.co.uk/sewn.html (2005).
Beiersdorf Inc., "Coverlet® Adhesive Dressings, Hospital Sizes (#1307 Used as N-G Holder)," product brochure (1990).
Biomedix, Inc., "EndoGrip™ Endotracheal Tube Holder," product brochure (1994).
Bird & Cronin, Inc., "Trach-Mate™ Tracheostomy Tube Holder," product information at http://www.birdcronin.com (2005).
Bruce Medical Supply, "Trach Tube Strap," product information at http://store.yahoo.com/brucemedical/trachtubestrap.html (2005).
Cooper Surgical, Inc., "COMFIT™ Endotracheal Tube Holder," product information at http://www.coopersurgical.com (2005).
Cooper Surgical, Inc. (Ackrad Laboratories, Inc.), "TRAKE-fit™," product brochure (1997).
Custom Hospital Products, "Cotton Twill (Trach Tape)," "Trach Ties with Velcro," and "Tracheostomy Tube Ties," product catalog (undated).
DHD Healthcare, "DHD® Endotracheal Tube Holder," product brochure (2001).
DHD Healthcare, "DHD® Ventilator Support: Tracheostomy Strap," product information at http://www.dhd.com/catalog/ventilator/tracheostomyStraps.asp (2005).
DHD Healthcare, "Ventilator Support: Endotracheal Tube Holder Wrap Strap," product information at http://www.dhd.com/catalog/ventilator/endostrap.asp (2005).
DHD Healthcare, "DHD® Wrap Strap™ Endotracheal Tube Holder," product brochure (2001).

Dale Medical Products, Inc., "Dale® hug Hospital Utility Grip, product sheet No. 930, holds tubes and cords securely" (1980).
Deknatel, a division of Howmedica, Inc., "Naso-Gard™ Nasogastric Tube Holder," product brochure (undated).
EMS Medical, "Breeze Happy Holder," "Breeze Tracheostomy Tube Holder," "Breeze St. Marina Safety Net," "Breeze Endotracheal Tube Holder," and "Breeze Wet Protect" product information at http://www.ems-medical.co.uk/breeze.php (2005).
Encompas™ Unlimited, Inc., "Bite Blocks," product information at http://www.encompasunlimited.com (2005).
Encompas™ Unlimited, Inc., "Adult Bite Block," product information at http://www.encompasunlimited.com/store (2005).
Encompas™ Unlimited, Inc., "Adult Best Block," product information at http://www.encompasunlimited.com (2005).
International Search Report for PCT/US2005/044200, dated Apr. 3, 2006, Ex. Martine Eich.
ErgoMed, Inc., "Tube Tamer" and "Tube Restraint" product information at http://www.ergomed.com/TubeSecuringDevices.html (2005).
ErgoMed, Inc., "The Tube Tamer® B7013" product brochure (undated).
ErgoMed, Inc., "Trakeez" and "Trach Tamer," product information at http://www.ergomed.com/TubeSecuringDevices.html (2005).
E-Med Corporation, "Flexi-Trak™ Anchoring Device" product brochure (undated).
Genetic Laboratories Wound Care, Inc., "Cath-Strip™ Reclosable Catheter Fastener" product brochure (undated).
Genetic Laboratories Wound Care, Inc., "NG Strip™ Nasal Tube Fastener," product brochure (undated).
Genetic Laboratories Wound Care, Inc., "Percu-Stay Large Catheter and Tube Anchoring Device," product announcement (undated).
Genetic Laboratories Wound Care, Inc., "UC Strip™ Catheter Tubing Fastener," product brochure (undated).
Hollister, "Oral Endotracheal Tube Attachment Device (ETAD)," product information at http://www.hollister.com/us (2005).
Hollister, "E•TAD Oral Endotracheal Tube Attachment Device" product brochure (undated).
Hudson RCI®, "Endotracheal Tube Holder," product brochure (1984) and product information at http://www.hudsonrci.com/Products (2005).
Hudson®, "Infant Nasal CPAP System," product brochure (1988).
Hy-Tape® International, "Hy-Tape®—The Original Pink Tape®," product information at http://www.hytape.com/hytape/Docs/endo.html (2005).
Kapitex Healthcare Limited, "Trachi-Hold tube holders," product information at http://www.kapitex.com/products/tracheostomy/products-trachi-hold1a.htm (2005).
R. Lewis, Inc., "Lewis Tube Holder™," product brochure (undated).
M.C. Johnson Co., Inc., "Cath-Secure® Multi-Purpose Tube Holder," product brochure and product wrappers (undated).
M.C. Johnson Co., Inc., "Cath-Secure®, New and Improved," product brochures (undated).
M.C. Johnson Co., Inc., "Cath-Secure Dual Tab™ Multi-Purpose Tube Holder," product brochures and product wrappers (undated).
M.C. Johnson Co., Inc., "NG Secure™ tube holder," product brochure (undated).
Marpac, Inc., "ET Adhesive Tape™," product information at http://www.marpac.biz/ettape.html (2005) and product brochure (2004).
Marpac, Inc., "Tracheostomy Collar™," product information at http://www.marpac.biz/collar.html (2004).
Marpac, "Tracheostomy Collar™" adult with twill/one size fits all, latex free, instructions, product packaging (undated).
Medex, "SecureEasy®," and "Quickstrap™," product brochure (undated) and product information at http:/www.medex.com/Medex/Product_Catalog/Respiratory/Products (2005).
Mor-Mac, Inc., "Tube Guard®," product brochure (1987).
N-C-N Products Co., "C-N Endotracheal Tube Holder," product brochure (undated).
Nellcor, "Tracheostomy Tube Holder," product description at http://www.nellcor.com (2005).

Nellcor, "Tracheal Tube Restraint," product information at http://www.nellcor.com (2005).
Olympic Medical, "Olympic Endo-Lok™ Endotracheal Tube Holder," product brochure (undated), and product description at http://www.olymed.com/endo-lok.htm (2005).
Paraproducts.com, "Grip-Et™ Endotracheal Tube Holder," product information at http://www.paraproducts.com (2005).
Pepper Medical, "Tracheostomy Tube Neckband," "Ventilator Antidisconnect Device & Tracheostomy Tube Neckband," "Pediatric Tracheostomy Tube Neckband," and "Laryngoscope Handle & Disposable Fiber-Optic Blades," product brochure (undated) and product information at http://www.peppermedical.com/distitems.html (2005).
Pepper Medical™, "Vent-Tie® #401," anti-disconnect device & trach-tube4 neckband, product packaging (Rev. Mar. 2004).
Pocket Nurse, "Adjustable Endotracheal Tube Holder," product brochure (undated).
Portex Limited/Smiths Industries Medical Systems, "Adult Oral Tracheal Tube Holder," product brochure (undated).
Portex Limited/Smiths Industries Medical Systems, "Portex Velcro® Tracheostomy Tube Holders," product information at http://www.portex.com (2005).
Posey Company, "Posey Foam Trach Ties," product information at http://www.posey.com (2005).
Precision Medical, "PM1110 Endotracheal Tube Holder," product information at http://www.precisionmedical.com/productpages/regaccess.asp (2004).
Rüsch, Inc., a Teleflex Company, "Soft Cushion Neck Band with adjustable velcro straps," product information at http://www.myrusch.com (2005).
Scott Specialties, Inc., "Scott Tube Holders," product brochure (undated).
Skil-Care™ Corporation, "Trach Tube Holders and Ties," product brochure (undated).
Tecnol, "Naso-Gastric Tube Holder" product brochure (undated).
STI Medical Products, "Thomas™ Endotracheal Tube Holder," product brochure (1999); and product information at http://www.stimedical.com/tube_holder.htm (2005).
STI Medical Products, "Thomas™ Tracheostomy Strap," product packaging (Feb. 1994).
TNT Moborg International Ltd., "Immobilé Sterile for Compliant Patient Line Control," product packaging (undated) and product advertising (1995).
Tecnol, Inc., "Secure-All™ Tube Holder," product brochures (undated) and "Tube-Control Plus™ with Hydrogel" product packaging (1994).
Trademark Medical Corporation, "Craig Tube Holder," product brochure (undated).
Transatlantic Handelsgesellschaft Stolpe & Co. mbH, "Transafix®," product brochure (1998).
Tyco Healthcare/Kendall, "Tracheostomy Care Trays," product information at http://www.kendallhq.com/catalog/printfriendly.asp (2004); Superior Healthcare Group, Inc. "tracheostomy care trays and tube holders" price list (1994); and "Tube Holder" product description (undated).
Venmark International, "NG Secure tube holder," product information (1995).
Welcon, Inc., "Trachtape® Endotracheal Tube Securing Device," "Economy Tracheostomy Tube Holder," and "Tracheostomy Tube Holder" product information at http://www.welcon.com/2700.htm (2005).
Welcon, Inc., "Trachtape™ Endotracheal Tube Securing Device," product brochure (undated).
XiMEDix, "Endo-Secure," product information at http://www.ximedix.com (2005); and product brochure (1996).
XiMEDix, "Trach-Secure™ Tracheostomy Tube Retaining Collar," product brochure (undated).
Zefon Medical Products, "K-Lok® Universal Securement Device," product packaging (undated).

\* cited by examiner

TRACHEOSTOMY TUBE HOLDER

CROSS-REFERENCE TO RELATED APPLICATIONS

This application claims priority to U.S. provisional application No. 60/548,406 filed on Feb. 27, 2004, the contents of which are hereby incorporated in its entirety by reference.

BACKGROUND

Insertion of a tracheostomy tube is a common procedure today in connection with patients who require assistance to breathe. It is essential to secure the tube to ensure that the tube does not accidentally dislodge or move relative to the patient. Accordingly, straps have been developed to hold the tracheostomy tube in place. For example, U.S. Pat. No. 4,331,144, herein incorporated by reference, discloses a band for supporting a tracheostomy tube. A similar band is shown in prior art FIG. 1, a band similar to which is also sold by Dale Medical Products, Inc., of Plainville, Mass. (Product No. 240).

The tracheostomy tube holder of FIG. 1 includes a band 1 including first and second straps 10 and 12 for securing tracheostomy tube 30. Each strap is of a three-part construction having a cotton-lined surface 14, a flexible foam layer 16, and an outer loop surface 18. Straps 10 and 12 each have a tab 20 and 22, respectively, attached thereto for threading through apertures 24 and 26 in the tracheostomy tube flange 28 that supports the tracheostomy tube 30.

As seen in FIG. 1, each tab 20 and 22 has Velcro hooks 32 on one side thereof for mating with the respective loop surface 18 on straps 10 and 12, thereby supporting the tracheostomy tube flange 28 and tube 30. Tabs 20 and 22 are preferably attached to straps 10 and 12 via stitching or other appropriate attachments means. Strap 12 also includes an elastic section 34 attached thereto, for example via stitching 35, to provide tension which ensures a secure fit around the patient's neck. Attached to elastic section 34 is a tab 36 (attached, for example, via stitching) having Velcro hooks on one side thereof for attachment to surface 18 of strap 10 (see, e.g., FIG. 3), and thereby securing: strap 12 to strap 10, the tracheostomy tube holder around the patient's neck, and the tracheostomy tube 30 in place.

One disadvantage of this prior art structure is that the ends 38 and 39 of straps 10 and 12 respectively, are in close proximity to the tracheostomy tube and the patient's stoma in the throat area, thereby exposing the end of the straps to secretions from the patient. Thus, the cotton surface 14 of the straps can quickly become saturated by fluids, thereby necessitating frequent replacement to maintain a clean environment. It would therefore be desirable to provide a tracheostomy tube holder which does not easily become saturated by patient fluids while still securely fastening the tracheostomy tube in place. It is further advantageous to provide a tracheostomy tube holder which is comfortable when used by the wearer, and which does not induce adverse dermatological effects such as redness, soreness, and irritation to the patient.

SUMMARY OF THE INVENTION

A tube holder is provided for securing a medical tube to a patient. In one illustrative embodiment, the tube holder includes a band to secure a medical tube to a patient, and first and second tabs attached at first and second ends of the band to secure the medical tube. Each of the first and second tabs include a hook surface and a loop surface, the hook surface and loop surface to mate with one another to secure the medical tube. The first and second tabs include moisture resistant material located on a surface contacting the patient's skin.

In accordance with another exemplary embodiment, a tube holder is provided which comprises a band to secure a medical tube to a patient, and first and second tabs attached at first and second ends of the band to secure the medical tube. Each of the first and second tabs includes moisture resistant material located on a surface contacting the patient's skin.

DETAILED DESCRIPTION

Figure 1:
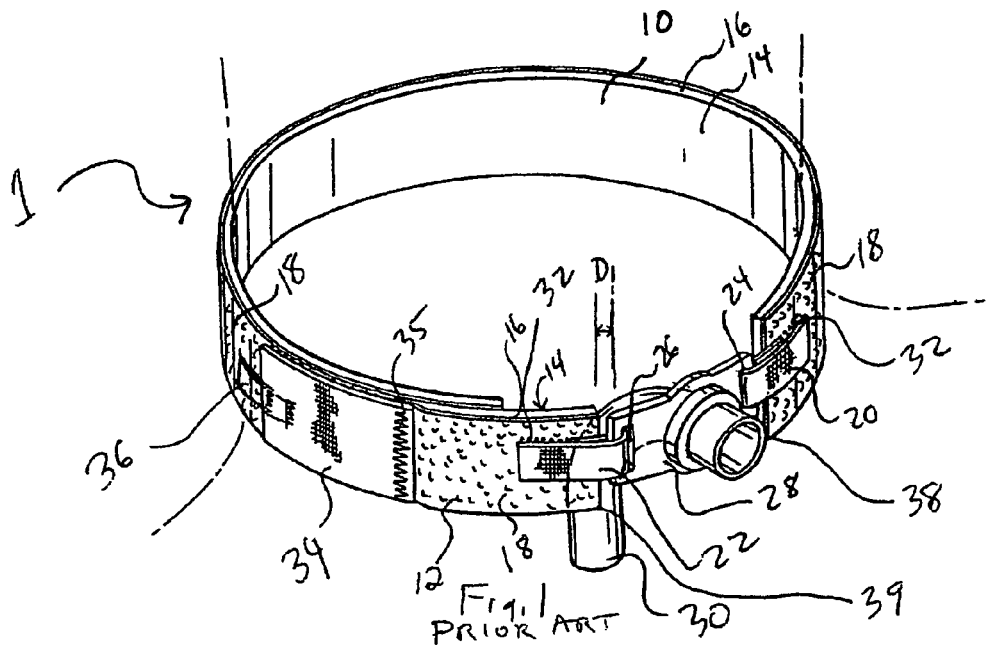
FIG. 1 is a perspective view of a prior art tracheostomy tube holder that shows the holder in-use securing a tracheostomy tube in place.
Figure 2:
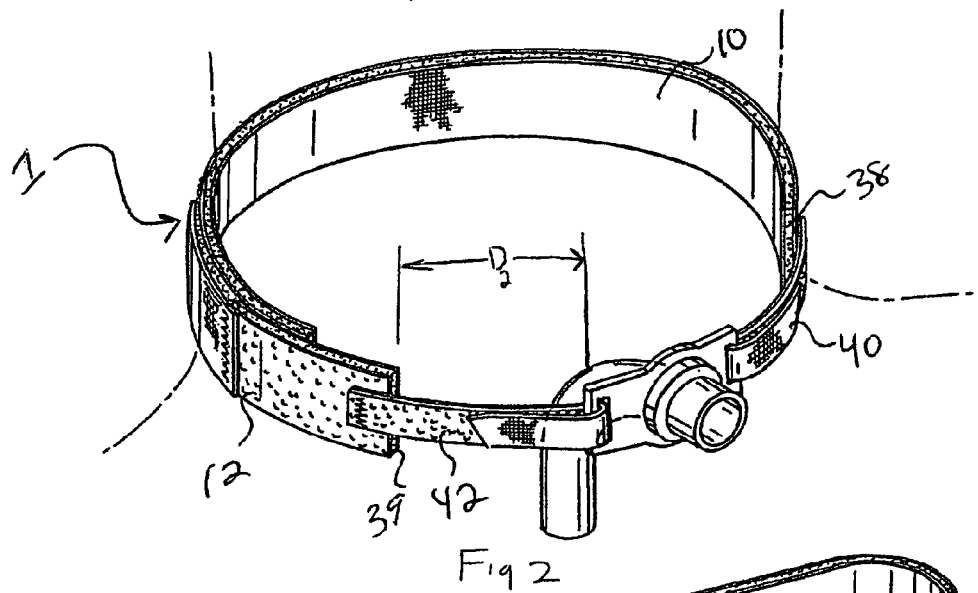
FIG. 2 is a perspective view of a tracheostomy tube holder according to one illustrative embodiment that shows the holder in-use securing a tracheostomy tube in place.
Figure 3:
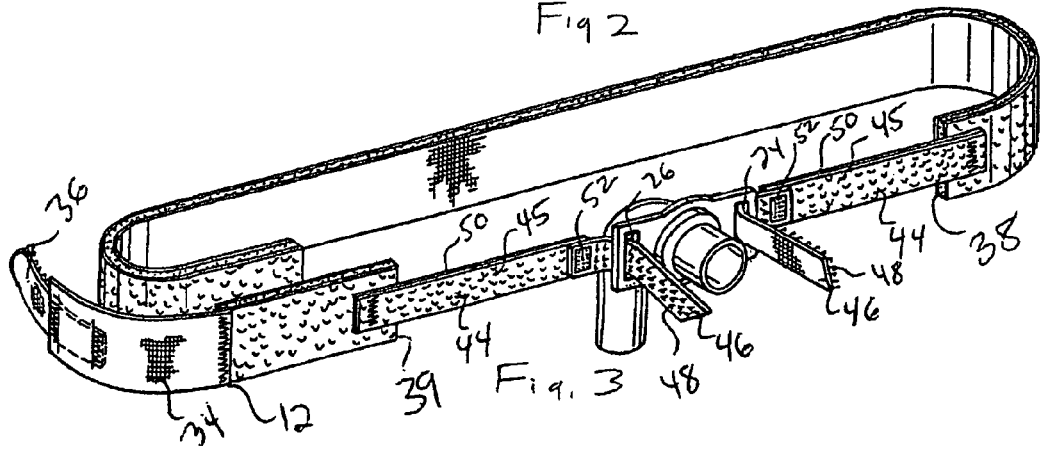
FIG. 3 is an exploded perspective view of the tube holder of FIG. 2.
Figure 4:
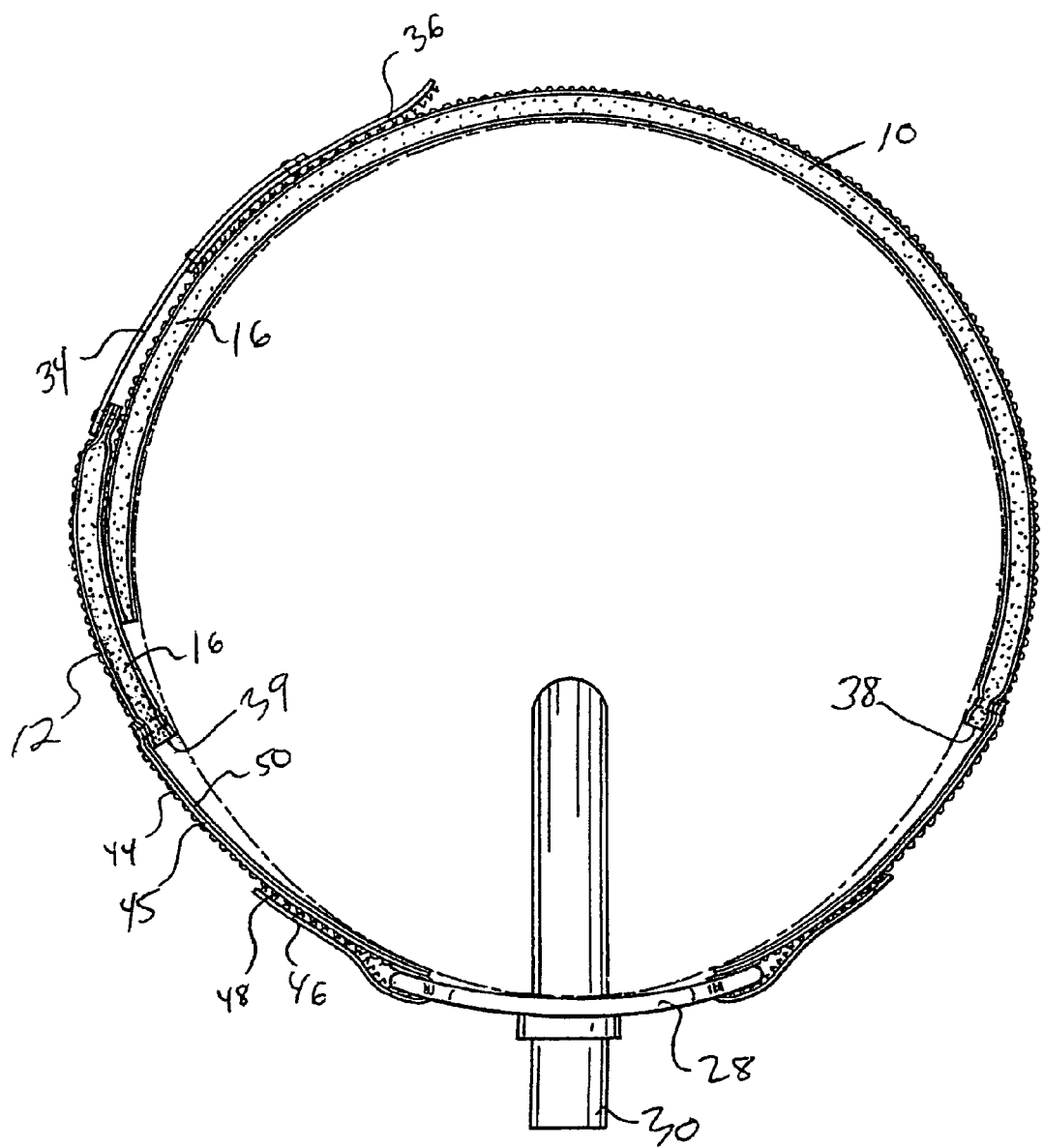
FIG. 4. is a top plan view of the tube holder of FIG. 2.

FIGS. 2-4 show a tracheostomy tube holder according to one illustrative embodiment consistent with principles of the present invention. The tracheostomy tube holder in FIGS. 2-4 is similar in some respects to the tube holder of FIG. 1, but includes tabs 40 and 42 attached to band 1. Reference characters from FIG. 1 are used to refer to similar elements of FIGS. 2-4.

The use of tabs 40 and 42 generally enable ends 38 and 39 of straps 10 and 12 to be distanced from the patient's throat and neck area to avoid saturation of these ends from fluid from the patient. Straps 40 and 42 both include a first section 44 attached to the end of straps 10 and 12, respectively, via, for example, stitching, sonic welding, or any appropriate attachment method. Section 44 includes loop material surface 45 on one side thereof. Tabs 40 and 42 each also include a second section 46 attached to section 44 to be threaded through apertures 24 and 26 when in use, as is shown in FIGS. 2 and 4. Tab 36 has a free end which includes rounded corners (see FIG. 3), or a rounded edge. This rounded, softened edge prevents snagging and inadvertent injury to the patient and/or the caregiver during placement and removal of the holder 1.

Section 46 includes a Velcro-type hook material 48 on one side thereof to mate with loop surface 45 on tabs 40 and 42 after being threaded through apertures 24 and 26, to secure the flange 28 and tube 30 in place. The hook material can be formed, for example, of molded plastic hooks. The loop material 45 is laminated to a moisture resistant material 50, which faces the patient during use, such as a plastic film. Section 46 is also preferably made of a moisture resistant material such as a plastic.

In one exemplary embodiment, this moisture resistant material can also be stainproof, windproof, resistant to fungus and viral penetration, and suitable for sterilization for use in medical applications. Further, the material can also be flexible, reusable, and fire retardant. In addition, the moisture resistant material can also be formed of an antibacterial material, or include an antibacterial material or coating. The plastic material should be of the type that can easily be applied to a woven, non-woven or knit fabric, and should have sufficient abrasion resistance, burst strength, and a low degradation rate suitable for its intended application. One example of a suitable moisture resistant material is a monolithic thermoplastic elastomer film sold under the trade name Spor-Tex. Section 46 can be attached to section 44 by any appropriate fastener 52, such as a sonic weld, heat seal, etc.

Accordingly, it can be seen that material susceptible to fluids from the patient, e.g., cotton surface 14 of straps 10 and 12, are significantly distanced from the stoma in the throat area of the patient around which fluids are produced. For example, this improvement is illustrated by a comparison of the distance (D1 of FIG. 1) between the end 39 of the cotton surface 14 and the flange 28 of the prior art, and the distance (D2 of FIG. 2) between the end 39 of the cotton surface 14 and the flange 28 of the foregoing illustrative embodiment.

While the straps 10 and 12 can be formed from cotton to ensure a soft, smooth surface contacts the patient's skin, as previously mentioned materials that resist water and moisture can be used as surface 50 of tabs 40 and 42. Nonwoven or woven materials can be utilized can be used, provided that the material is also moisture resistant, or repels moisture. In addition to Spor-Tex material previously mentioned, an additional suitable material, for example, is Suprel™, a bi-component material comprising polyester and polyethylene from DuPont™. Another suitable material, for example, is Goretex®. Such waterproof materials could provide a more comfortable feel for the user, since the moisture resistant material creates a cooling effect by preventing the wearer from experiencing dampness due to patient fluids that may be retained in the surface 50 against which the patient's skin is in contact.

Further, the tabs 40 and 42 resist the absorption of patient fluid such as blood, perspiration, etc., to thereby prevent the tabs from acting as a medium for infection. Tabs 40 and 42 also advantageously prevent moisture from collecting onto the tracheostomy tube holder 1 by physically distancing the water-absorbable components of the holder 1 away from the tube 30. For example, in prior art FIG. 1, end 39 is almost contacting the flange 28, while in FIG. 2 end 39 is significantly distanced, for example by about a half inch or greater, and preferably about one inch, and more preferably about two inches. Thus, tabs 40 and 42 of the foregoing illustrative embodiment enable the tracheostomy tube holder of FIGS. 2-4 to be less susceptible to fluids and thereby cleaner and necessitating less frequent changing.

The aforementioned moisture resistant materials that form surface 50 of tabs 40 and 42 are also smooth and not prone to irritate the skin of the patient, unlike other materials typically used in such holders, such as woven nylon without a smooth backing for contacting the patient's skin. Thus, tabs 40 and 42 not only have a skin-contacting surface 50 that is moisture resistant but also smooth to prevent irritation of the patient's skin.

In an alternative embodiment, instead of two straps 10 and 12, a single strap can be used having tabs 40 and 42 attached on either side. The single strap preferably includes an elastic portion that is integrally disposed therein. The elastic portion can be formed, for example, of an elastic fabric web similar to section 34 of FIG. 2.

Figure 5:
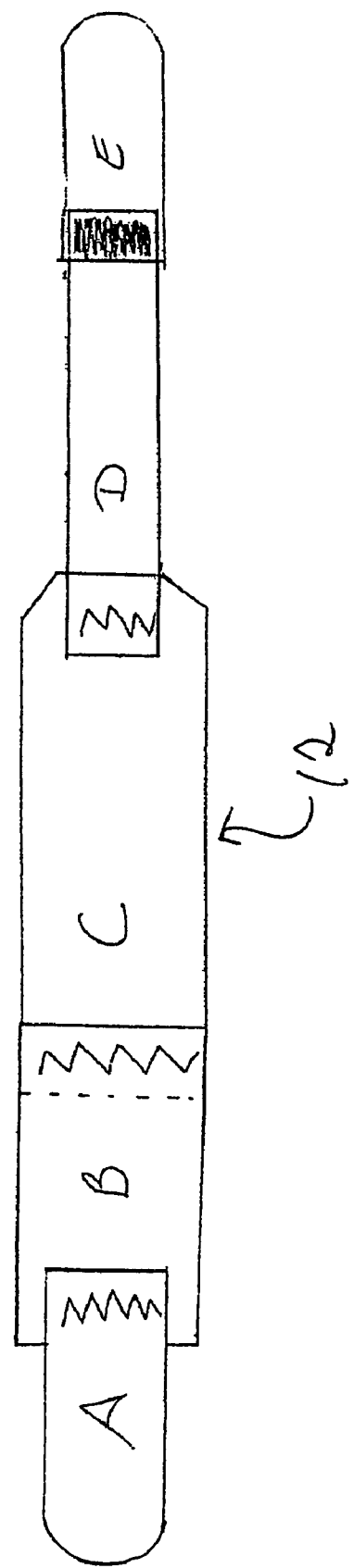
FIG. 5 is a top plan view of an alternative illustrative embodiment of a tracheostomy tube holder.

FIG. 5 shows an alternative illustrative embodiment showing a slightly different construction of strap 12, in which section A can comprise hooks, section B can comprise an elastic fabric web material, sections C and D can comprise a nylon loop material having a laminated film backing such as, e.g., Spor-Tex, and section E can comprise a plastic hook material with a moisture resistant backing. Sections A, B, C, and D are attached to one another by stitching, while section D is fused to section E, though any appropriate fastening method can be used. While sections A, B, D, and E of strap 12 remain substantially the same as the embodiment described above with reference to FIGS. 2-4, section C is constructed of the same material as section D (section 44 described above); that is, a moisture resistant material having a loop surface laminated thereto replaces the cotton surface 14 and a foam layer 16 of strap 12.

Figure 6:
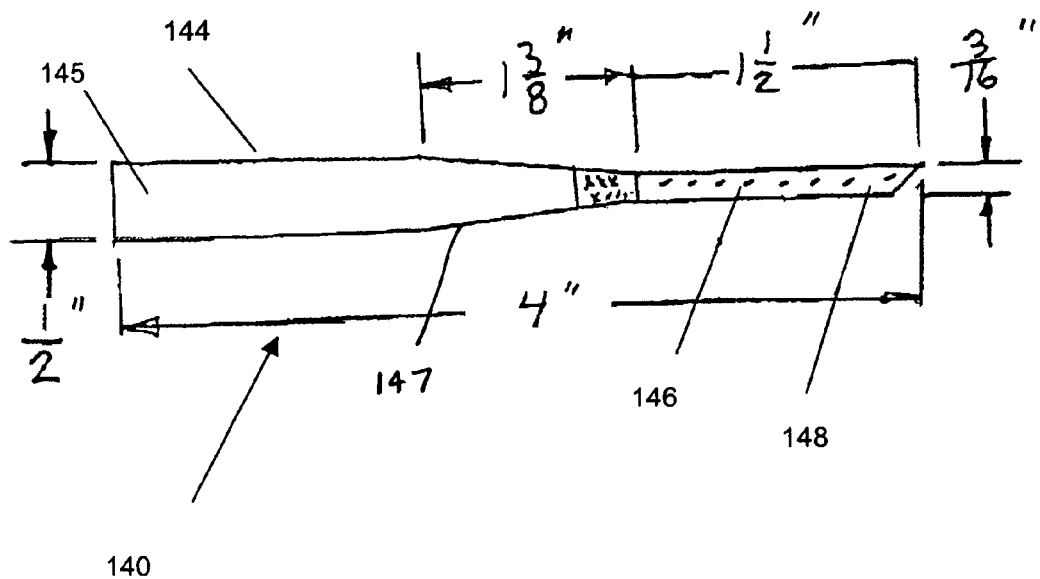
FIG. 6 is a top plan view of an alternative illustrative embodiment of a tab for a tracheostomy tube holder.
Figure 7:
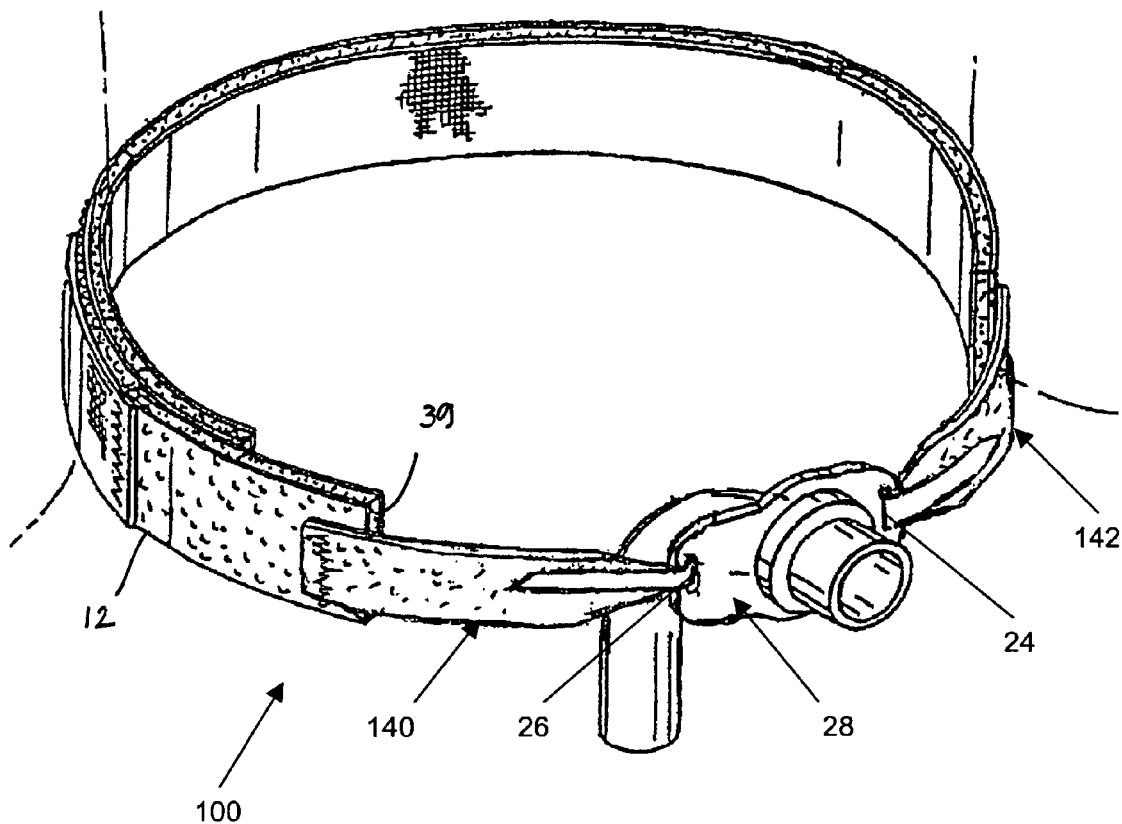
FIG. 7 is a perspective view of an alternative illustrative embodiment of a tracheostomy tube holder that utilizes the tab of FIG. 6, shown securing a tracheostomy tube in place.

FIGS. 6 and 7 show a tapered tab 140 and a tracheostomy tube holder 100 according to another illustrative embodiment consistent with principles of the present invention. The tracheostomy tube holder 100 is similar in some respects to the tube holder of FIG. 1, but includes tapered tabs 140 and 142 attached to band 1. Reference characters from FIG. 1 are used to refer to similar elements of FIGS. 6 and 7.

As shown in FIG. 6, tab 140 has a tapered shape that gradually narrows from first section 144 to second section 146. First section 144 can include a loop material 145 while second section 146 can include a Velcro-type hook material 148, similar to the embodiments previously described. First section 144 can be fastened to second section 146, for example, by sonic welding. In one embodiment, the first section 144 can be about ½ inches wide, and taper down to the second section 146 which can be about 3/16 to ¼ inches wide. The overall length of the tab 140 can be about 3 to 4 inches long, while the overall length of the second section 146 can be about 1 and a half to 2 inches long, with the tapered portion 147 being about 1⅜ to 1 and a half inches long. It should be noted that the foregoing dimensions are exemplary only, and the invention is not limited to the specific dimensions stated herein.

The second section 146 enables insertion into small slots such as those found in children's sized tracheostomy tube flanges. Moreover, the tapered tab design provides a snug fit with the slots 24, 26 in the tube flange 28 of the tracheostomy tube, as shown in FIG. 7.

Figure 8:
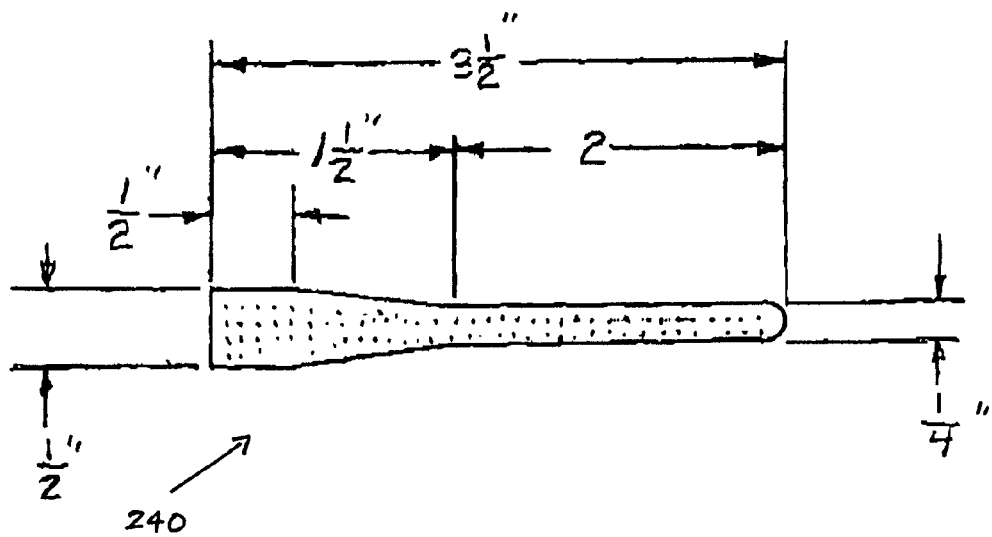
FIG. 8 is a top plan view of another alternative illustrative embodiment of a tracheostomy tube holder tab.

FIG. 8 shows another alternative tapered tab design. Tapered tab 240 is formed of a one-piece die cut plastic with molded Velcro hooks on one surface and a smooth, moisture resistant surface on the opposite surface. A plastic such as nylon is an appropriate material for tab 240.

Figure 9A:
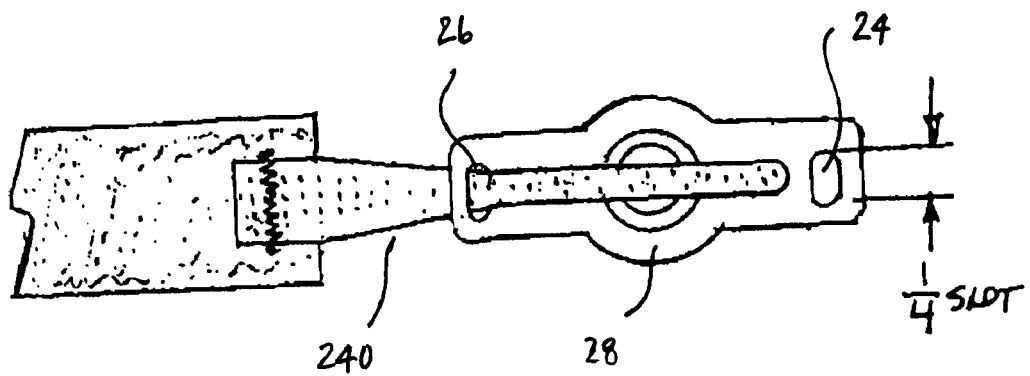
FIG. 9A is a perspective view of the tracheostomy tube holder tab of FIG. 8 in use with a tube flange.
Figure 9B:
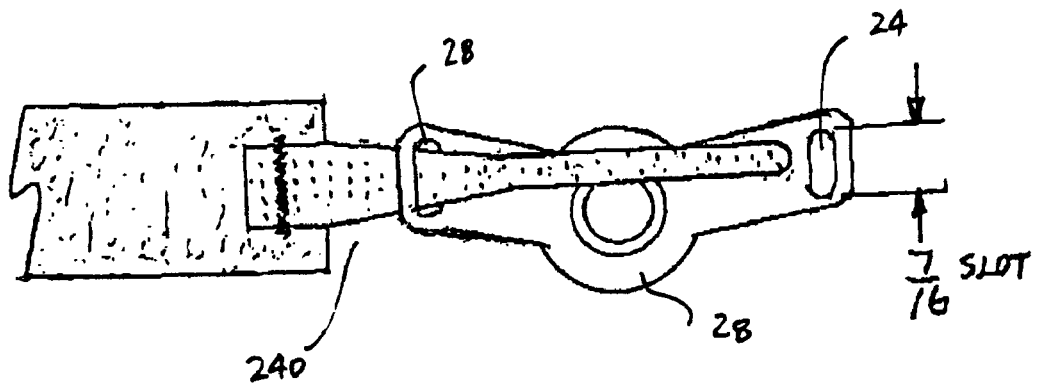
FIG. 9B is another perspective view of the tracheostomy tube holder tab of FIG. 8 in use with a tube flange.
Figure 9C:
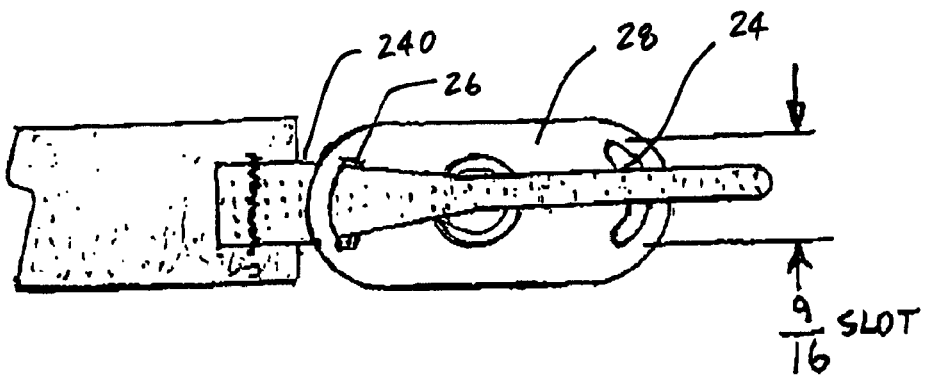
FIG. 9C is still a further perspective view of the tracheostomy tube holder tab of FIG. 8 in use with a tube flange.

An advantage of the tapered tabs 140, 240 is that the tapered design helps stabilize the tracheostomy tube by preventing twisting or rotation of the tube flange 28 when in use. For example, as shown in FIG. 9A, the tapered one-piece tab 240 shown in FIG. 8 is used with a tube flange 28 having a ¼ inch slot. The tapered design enables a taper lock and snug fit between tab 240 and the slot 26 once the tab 240 is folded over the slot 26. Similarly, as shown in FIGS. 9B and 9C, the tab 240 can also form a taper lock and snug fit with tube flanges 28 that have either a 7/16 inch slot 26 (FIG. 9B) or a 9/16 inch slot 26 (FIG. 9C), by further threading the tab through the slot. Accordingly, torqueing and pivoting motion is essentially prevented with the tapered tab 240 construction and enables the tracheostomy tube holder to be used with a variety of sized tube flanges 28.

Figure 10A:
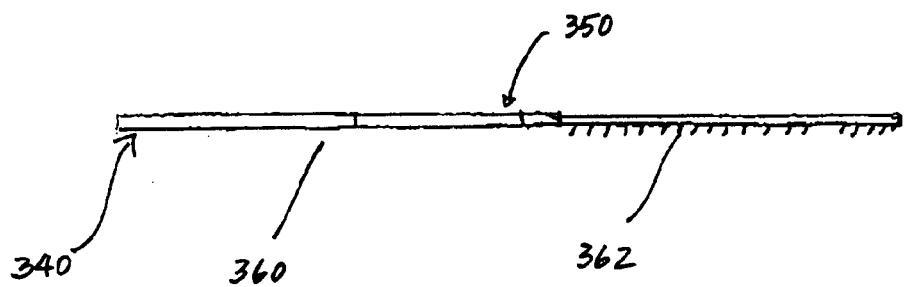
FIG. 10A is a side view of another alternative illustrative embodiment of a tracheostomy tube holder tab.
Figure 10B:
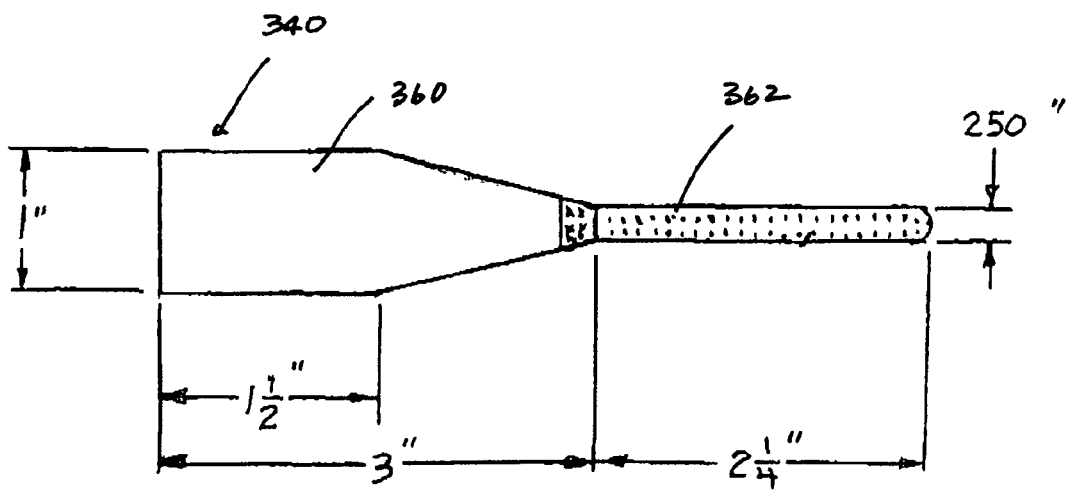
FIG. 10B is a top plan view of the tracheostomy tube holder tab of FIG. 11A.
Figure 11:
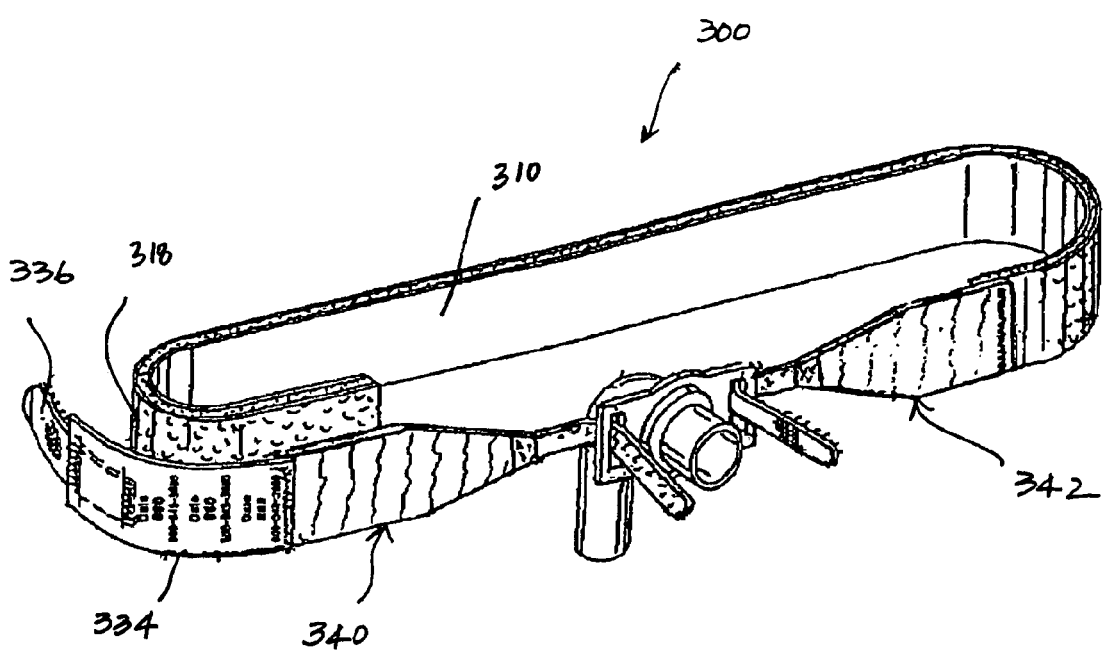
FIG. 11 is a perspective view of another illustrative embodiment of a tracheostomy tube holder that utilizes the tab of FIGS. 10A and 10B, shown securing a tracheostomy tube in place.

Another illustrative embodiment of a tracheostomy tube holder 1 consistent with the principles of the present invention is shown in FIGS. 10A, 10B and 11. As shown in FIGS. 10A and 10B, the tab 340 has a tapered design similar to tabs 140, 240. Tab 340 includes a first segment 360 having a loop surface attached to a second segment 362 having a hook surface for mating engagement with the looped surface of segment 360. The first and second segments 360, 362 can be attached to one another by any suitable mechanism, such as for example, a weld joint. Exemplary dimensions are shown in FIG. 10B wherein the tab 340 ranges from one inches at one end of first segment 360 to 1/4 inches thick at the opposite end on second segment 362. Additionally, the tab 340 can have a back surface 350 comprising a moisture resistant material such as, for example, Spor-Tex. Either the first segment 360 or the second segment 362, or both segments of tab 340, can include the moisture resistant material on a back surface. In one embodiment, the Spor-Tex material can be welded to both segments 360 and 362 to provide a moisture resistant backing. As shown, the second segment 362 of tab 340 includes a rounded end which reduces snag or injury to the patient or caregiver.

Tabs 340, 342 are shown in a tracheostomy tube holder 300 of FIG. 12, wherein tabs 340 and 342 are shown on either side of the stoma site. Tab 340 can be attached to an elastic fabric web 334 which can include a tab 336 with Velcro hooks on one side thereof for attachment to surface 318 of strap 310. Tab 342 can be attached directly to strap 310, such as by stitching. The double tabs 340 and 342 on either side of the stoma site enables the user to bring the band 310 closer if necessary to the tube flange while still providing a smooth, fungus resistant, antiviral, antibacterial moisture resistant surface near the stoma site.

Having thus described certain embodiments of the present invention, various alterations, modifications, and improvements will readily occur to those skilled in the art. Such alterations, modifications, and improvements are intended to be within the spirit and scope of the invention. For example, it should be noted that the foregoing principles of the present invention can be applied to all types of medical tubes in addition to tracheostomy tubes, in which it is desirable to distance a moisture susceptible section of the holder from the tube being held, such as endotracheal tubes, naso-gastric tubes, catheters, intravenous tubes, etc. Accordingly, the foregoing description is by way of example only, and not intended to be limiting.

What is claimed is:

1. A tube holder for securing to a patient a flange for a medical tube, the flange having a first slot and a second slot at opposite ends, each slot being an elongated opening having a length, the tube holder comprising:
a band to attach to the patient's body, the band having first and second band ends; and
first and second tabs, each having a first end and a second end, the first end of the first tab and the first end of the second tab respectively for attaching to the first band end and the second band end, the first and second tabs including moisture resistant material located on a surface configured to contact the patient's skin, wherein the second end of the first tab and the second end of the second tab each include a tapered region having a wide end and a narrow end and having a gradual taper from a first width at the wide end to a second width that is smaller than the first width at the narrow end, wherein the length of the first slot and the length of the second slot each is smaller than the first width and larger than the second width, such that when the tube holder is securing the flange to the patient, the first slot and the second slot are threaded through by the second end of the first and the second tabs respectively, the first slot being fitted with a first slot-fitting section of the tapered region of the first tab, the first slot-fitting section located between and not at either the wide end or the narrow end of the tapered region of the first tab, and the second slot being fitted with a second slot-fitting section of the tapered region of the second tab, the second slot-fitting section located between and not at either the wide end or the narrow end of the tapered region of the second tab, wherein a width of the first slot-fitting section is about equal to the length of the first slot, and wherein a width of the second slot-fitting section is about equal to the length of the second slot, to prevent twisting or rotation of the first and second tabs when fitted with the first and second slots respectively.

2. The tube holder of claim 1, wherein the moisture resistant material comprises a laminated plastic film.

3. The tube holder of claim 1, wherein the moisture resistant material forms a back surface of the first and second tabs.

4. The tube holder of claim 1, wherein the first and second tabs each include a first mating section comprising loops and a second mating section comprising hooks configured to mate with the loops to secure the tube in place, the moisture resistant material being located on the first mating section of each tab.

5. The tube holder of claim 1, wherein the moisture resistant material is resistant to fungus, viral penetration, or bacteria.

6. The tube holder of claim 1, wherein the moisture resistant material has a smooth surface so as to be non-irritating to the patient.

7. The tube holder of claim 1, wherein the band is comprised of a material not resistant to moisture.

8. The tube holder of claim 1, wherein each of the first and second tabs further include hook-type material on a surface opposite to the side configured to contact the patient's skin, and the first and second tabs are formed from a one-piece material.

9. The tube holder of claim 8, wherein the moisture resistant material is smooth to prevent irritation to the patient's skin.

10. The tube holder of claim 1, wherein the second ends of the first and the second tabs each include a chamfered, beveled, or rounder distal tip which is separate from the corresponding tapered regions.

11. The tube holder of claim 1, wherein the first width is around 9/16 inches and the second width is around 1/4 inches.

12. The tube holder of claim 1, wherein when the tube holder is securing the flange to the patient, the first slot and the tapered regions of the first tab, and the second slot and the tapered region of the second tab each form a snug fit, which prevents twisting and rotation of the flange.

13. The tube holder of claim 1, wherein first and second tabs are each die-cut in one piece.

14. A tube holder for securing to a patient a flange for a medical tube, the flange having a first slot and a second slot at opposite ends, each slot being an elongated opening having a length, the tube holder comprising:
- a band to attach to the patient's body, the band having first and second band ends, and further having a first joining section and a second joining section, the first joining section including a loop material and the second joining section including a hook material, such that the first and second joining sections can be adjustably joined to adjust the length of the band; and
- first and second tabs, each having a first end and a second end, the first end of the first tab and the first end of the second tab respectively for attaching to the first band end and the second band end, the second end of the first tab and the second end of the second tab each including a tapered region having a wide end and a narrow end and having a gradual taper from a first width at the wide end to a second width that is smaller than the first width at the narrow end, wherein the length of the first slot and the length of the second slot each is smaller than the first width and larger than the second width, and the length of the band is adjusted such that when the tube holder is securing the flange to the patient, the first slot and the second slot are threaded through by the second end of the first tab and the second end of the second tab respectively, the first slot being fitted with a first slot-fitting section of the tapered region of the first tab and the second slot being fitted with a second slot-fitting section of the tapered region of the second tab, the first and the second slot-fitting sections respectively located between and not at either the wide end or the narrow end of the tapered region of the first and the second tab, wherein a width of the first slot-fitting section is about equal to the length of the first slot, and wherein a width of the second slot-fitting section is about equal to the length of the second slot.

15. The tube holder of claim 14, wherein each of the first and second tabs further include hook-type material on a surface opposite to a side of the corresponding tab configured to contact the patient's skin, and the first and second tabs are formed from a one-piece material.

16. The tube holder of claim 15, wherein the side of the first and second tabs for contacting the patient's skin is a smooth surface.

17. The tube holder of claim 14, wherein the first and second tabs each include a first securing section comprising loops and a second securing section comprising hooks and having a length such that when the first and second tabs engage opposing tracheostomy tube flanges the first securing section of each tab comprising loops can be secured to the second securing section comprising hooks such that the band first and second ends are spaced from the tracheostomy tube to prevent moisture on or around the tube from contacting the band.

18. The tube holder of claim 14, wherein the first and second tabs provide a tapered fit engagement with slots of a tracheostomy tube to prevent torquing and pivoting motion of the tube.

19. A method for securing to a patient a flange for a medical tube using a tube holder, the flange having a first slot and a second slot at opposite ends, each slot being an elongated opening; the tube holder including a band to attach to the patient's body, the band having first and second band ends, and first and second tabs, each having a first end and a second end, the first end of the first tab and the first end of the second tab respectively attached to the first band end and the second band end, further the second end of the first tab and the second end of the second tab each including a tapered region having a wide end and a narrow end and the tapered region having a gradual taper from a first width at the wide end to a second width that is smaller than the first width at the narrow end, wherein the length of the first slot and the length of the second slot each is smaller than the first width and larger than the second width, the method comprising:
- threading the second end of the first and the second tabs respectively through the first and the second slot; and
- securing the flange to the patient by fitting into the first slot a first slot-fitting section in the tapered region of the first tab and fitting into the second slot a second slot-fitting section of the tapered region of the second tab, wherein a width of the first slot-fitting section is smaller than the first width and larger than the second width and is about equal to the length of the first slot, and wherein a width of the second slot-fitting section is smaller than the first width and larger than the second width and is about equal to the length of the second slot, and wherein the first and the second slot-fitting sections are respectively located between and not at either the wide end or the narrow end of the tapered region of the first and the second tab.

* * * * *